United States Patent [19]

Mays et al.

[11] Patent Number: 4,863,719

[45] Date of Patent: Sep. 5, 1989

[54] MICROBIAL PRODUCTION OF POLYFRUCTOSE

[76] Inventors: Thomas D. Mays, 9774 Early Spring Way, Columbia, Md. 21046; Ellen L. Dally, 5705 Cedar La., Columbia, Md. 21044

[21] Appl. No.: 232,830

[22] Filed: Aug. 16, 1988

Related U.S. Application Data

[60] Division of Ser. No. 780,595, Sep. 26, 1985, Pat. No. 4,769,254, which is a continuation-in-part of Ser. No. 689,238, Jan. 4, 1985.

[51] Int. Cl.⁴ .................. A61L 9/04; A61K 7/32; A61K 7/16
[52] U.S. Cl. ...................................... 424/45; 424/49; 424/65; 514/777
[58] Field of Search .............. 424/45, 49, 65; 514/777; 435/94, 97

[56] References Cited

U.S. PATENT DOCUMENTS

| | | | |
|---|---|---|---|
| 3,033,758 | 5/1962 | Kaufmann et al. | 435/94 |
| 4,097,604 | 6/1978 | Thiele | 424/49 |
| 4,224,307 | 9/1980 | Thiele et al. | 424/49 |
| 4,335,207 | 6/1982 | Heady | 435/94 |
| 4,356,262 | 10/1982 | Heady | 435/97 |
| 4,478,936 | 10/1984 | Herlihy | 424/65 |
| 4,536,387 | 8/1985 | Sakamoto et al. | 514/777 |
| 4,642,111 | 2/1987 | Sakamoto et al. | 514/777 |

Primary Examiner—Marianne Cintins

[57] ABSTRACT

A water-soluble levan having a weight average molecular weight of about 10,000–40 million, preferably about 5–25 million and especially about 10–20 million which stabilizes a bovine serum albumin colloid having index (EAI) of about 3–100 determined according to the formula $EAI = 2T/OC$ wherein T is turbidity measured at 500 nm, C is the weight of emulsified protein per unit volume of the aqueous phase, and O is the volume fraction of a dispersed oil phase is produced by fermenting a nutrient growth medium feedstock having a carbon source consisting essentially of an assimilable sugar selected from the group consisting of sucrose, raffinose, or a mixture thereof with a microorganism capable of converting at least 50% of the fructose value of the sugar to said levan under nutrient growth conditions which enhance levan production while suppressing ethanol production, It is useful as a colloid stabilizing agent, particularly with foods, beverages, pharmaceuticals, dentifrices, and cosmetics.

15 Claims, 4 Drawing Sheets

DRAINAGE FROM EGG WHITE FOAMS

FIG. 1

FIG. 4

DRAINAGE RATES OF FOAMS PREPARED WITH BSA AND LEVAN

MICROBIAL PRODUCTION OF POLYFRUCTOSE

CROSS-REFERENCE TO RELATED APPLICATIONS

This application is a divisional application of U.S. patent application Ser. No. 06/780,595 filed Sept. 26, 1985 and now U.S. Pat. No. 4,769,254, which in turn is a continuation-in-part of U.S. patent application Ser. No. 06/689,238 filed Jan. 4, 1985, the contents of which are incorporated by reference herein.

DESCRIPTION OF THE INVENTION

1. Technical Field of the Invention

This invention relates to a water-soluble, essentially uncharged levan polymer which has useful emulsifying and thickening properties comparable to those of gum arabic, and to methods for the production and use thereof as well as compositions containing said levan polymer as an emulsifying agent. More particularly, this invention relates to the production of levan through the action of levan sucrose produced by an improved and modified bacterial strain of Zymomonas mobilis.

2. Background Art

Hydrocolloids, particularly polysaccharide gums, are widely employed in the food industry to stabilize disperse foods such as emulsions and foams (e.g. ice cream, whipped toppings, beer, salad dressings, sausages, etc.) see S. C. Sharma, Gums and Hydrocolloids in Oil Water Emulsions, J. Food Tech. January 1981, 59–67. These foods are polydisperse colloidal systems and are generally thermodynamically inherently unstable, i.e. in the absence of specific stabilizing agents such as polysaccharides the physical state of the processed food rapidly deteriorates. For example, ice creams develop ice crystals and become grainy, salad dressings separate, and sausages both exude oil and exhibit syneresis or weeping. The precise role of the polysaccharide is not well established in complex foods in which they are used; however, their ability in model systems to modify both the bulk properties of the continuous aqueous phase and the interfacial behavior of other components, particularly proteins, is considered indicative of their beneficial effects.

Levan or anhydrofructosylfructoside is a linear polymer of adjacent fructose residues covalently bonded together in the beta conformation between the 2- and 6- carbon atoms (E. A. Dawes et al., Biochem. J. 98: 804–812, 1966.) This polymer can be formed by the microbial fermentation of sucrose through a transfructosylation reaction catalyzed by the enzyme levan sucrase (E.C. 2.4.1.10). Several strains of bacteria have been described which elaborate a functional levan sucrase. These include strains of *Actinomyces viscous, Aerobacter levanicum, Acetobacter suboxydans, Bacillus licheniformis, Bacillus macerans, Bacillus subtilus, Gluconobacter oxydans, Streptococcus salivarius, Streptococcus mutans, Leuconostoc mesenteroides, Erwinia herbicola* and *Zymomonas mobilis*. Levan can also be formed in vitro by the action of levan sucrase on either sucrose or raffinose which functions as a fructosyl donor and an aldose molecule which acts as the fructosyl acceptor.

Levan has been used as an immunologic suppressor (Experientia 34: 1362–1363, 1978 and J. Pathol. 125: 103, 1978) and an immunogenic hapten conjugate (J. Dent. Res. 55: 129, 1976 and Moreno, U.S. Pat. No. 4,260,602). UK Patent Application GB 2,046,757-A published Nov. 19, 1980 describes a low cariogenic food sweetener prepared by subjecting a substrate solution containing aldose and sucrose or raffinose to the activity of levan sucrase, but the desired product is a trisaccharide and not a high molecular weight levan, which has not heretofore been to provide functional properties to food products.

Traditionally, small quantities of levan have been produced by the bacterial fermentation of sucrose, usually by a strain of *Actinomyces viscous* or *Aerobacter levanicum*. Levan produced by the in vitro activity of levan sucrase has been reported by T. Tanaka et al. in J. Biochem. 87 (1): 297–303 (1980). The applications of recombinant DNA technology have been applied in the in vitro genetic transfer of the sacB gene from *Bacillus subtilis* into a strain of *Escherichia coli* (J. Bacteriol. 153: 1424–31, 1983.) These processes, however, do not represent efficient means for the production of levan. In particular, the in vitro enzymatic synthesis of levan from sucrose would appear to be difficult in terms of producing a high molecular weight molecule, as evidenced by UK Patent Application GB 2,046,757-A.

The in vivo production of levan has also been described, e.g. in Jeanes et al. U.S. Pat. No. 2,673,828; Gaffar et al. U.S. Pat. No. 3,879,545; Ayerbe et al. U.S. Pat. No. 4,399,221; and E. A. Bodie et al., Appl. Environ. Microbiol. 50(3):629–633 (1985) the contents of which are incorporated by reference herein. Such methods have generally employed aerobic fermentation techniques in the presence of relatively small amounts of sucrose (i.e., less than about 2%) in the feedstock and have achieved relatively low yields.

DISCLOSURE OF THE INVENTION

Accordingly, it is a general object of the present invention to provide colloid systems which are stabilized by an effective amount of a water-soluble levan having a molecular weight of about 10,000–40 million, preferably about 5–25 million and especially about 10–20 million as determined by gel filtration chromatography and 300–1500 million, preferably 600–1200 million and especially about one billion as determined by light scattering and which characteristically stabilizes a bovine serum albumin emulsion having an emulsion activity index (EAI) of about 3–100, preferably about 10–50 and especially of at least 20, determined according to the formula $EAI = 2T/OC$ wherein T is turbidity measured at 500 nm, C is the weight of emulsified protein per unit volume of the aqueous phase, and O is the volume fraction of a dispersed oil phase.

Another object of the present invention is to provide such stabilized colloidal systems in the form of an emulsion, aerosol, or foam wherein the colloidal components are admixed with an effective amount of a levan stabilizing agent according to the present invention.

An additional object of the present invention is to provide a process for forming a stable emulsion of a water-insoluble or water-immiscible compound in water by admixing said compound with water, an emulsifying agent, and a stabilizing amount of a levan according to the present invention to provide emulsions having improved stability.

Yet another object of the present invention is to provide a process for forming a stable colloidal aerosol of a liquid dispersed in a gas by admixing said components with a suitable colloid forming agent and a stabilizing amount of a levan according to the present invention to provide aerosols having improved stability.

A further object of the present invention is to provide a process for forming a stable colloidal foam of a gas dispersed in a liquid by admixing said components with a foaming agent and a stabilizing amount of a levan according to the present invention to provide foams having improved stability.

A more particular object of the present invention is to provide stable emulsions of foods and beverages, particularly protein emulsions such as protein-air colloids or whipped protein food products.

Yet an additional object of the present invention is to provide levan polymers having a molecular weight in excess of 100 million as determined by light scattering.

Still another object of the present invention is to provide a biologically pure, stable in vitro culture of a microorganism from the genus Zymomonas which has been adapted to ferment sucrose or raffinose in a fermentation culture medium containing assimilable sources of carbon and nitrogen to form a levan product which is useful according to the present invention.

BRIEF DESCRIPTION OF THE DRAWINGS

The above and other objects, features, and advantages of the present invention will become more fully apparent to those skilled in the art to which this invention pertains from the following detailed description, taken in conjunction with the annexed drawings, wherein:

FIG. 1 plots the drainage of whipped egg white foams against whipping time and drainage time to illustrate the sensitivity of the method used herein for determining emulsion activity and stability;

FIG. 2 shows the effect of levan on the emulsion activity index (EAI) of bovine serum albumin (BSA);

FIG. 3 illustrates the effect of levan on the emulsion stability of bovine serum albumin; and FIG. 4 illustrates representative drainage rates of foams prepared with BSA and levan according to the present invention.

BEST MODE FOR CARRYING OUT THE INVENTION

Briefly, the above and other objects, features and advantages of the present invention are attained in one aspect thereof by providing new techniques for the preparation and use of a water-soluble levan having a weight average molecular weight of about 10,000–40 million, preferably about 5–25 million and especially about 10–20 million as determined by gel filtration chromatography and 300–1500 million, preferably 600–1200 million and especially about one billion as determined by light scattering and which is further characterized by stabilizing colloids such as bovine serum albumin oil emulsions having an emulsion activity index (EAI) of about 3–100, preferably about 10–50 and especially of at least 20, determined according to the formula EAI=2-T/OC wherein T is turbidity measured at 500 nm, C is the weight of emulsified protein per unit volume of the aqueous phase, and O is the volume fraction of a dispersed oil phase. While higher EAI values of up to about 200 can be obtained, they are undesirable because the emulsion stability is generally reduced to unacceptably low levels.

While described in detail with respect to the presently preferred embodiment of a colloidal foam system of air in protein such as egg white or BSA, it will be appreciated by those skilled i the art to which this invention pertains that the levan of the present invention can be used to stabilize diverse types of colloidal systems including sols (dispersions of solid in liquid), emulsions (dispersions of liquids in liquids), aerosols (dispersions of liquids or solids in gases), foams (dispersions of gases in liquids or solids), and gels (dispersions in which one component provides a structural framework with other components filling the interstitial spaces therein).

In one aspect, the present invention provides a new method for the preparation of such levans. In accordance with this aspect, a levan-producing microorganism is acclimated to grow anaerobically on a culture medium having as the sole source of assimilable carbon atoms one or more sources of the sugars sucrose, raffinose, or mixtures thereof at increasingly high concentrations of from at least about 2% up to about 40% of such sugar, generally at least 5% and preferably about 10–15%.

The culture medium contains a suitable source of assimilable nitrogen atoms, but in amounts less than half that normally required when being grown for ethanol production, preferably less than one-fourth of such amount. Vitamin requirements such as pantothenic acid, biotin, thiamine, pyridoxine, and nicotinic acid can be provided as yeast extract components or separately. Additionally, fermentation is carried out at temperatures below those employed in ethanol production, generally at least 5° C. and preferably at least 10° C. lower, thereby further favoring the microorganism's metabolism in favor of producing levan from sucrose.

Optimal results to date have been achieved within the above parameters for *Zymomonas mobilis* by first passing the inoculum seed culture 3–4 times in a culture medium containing sucrose as the sole carbon source at concentrations of preferably 10–15%. A suitable yeast extract is employed as the sole nitrogen source at concentrations of only about 0.25%, since in some instances levan production has been observed to drop at only 0.5% (yeast extract is generally used at concentrations of 1–2% for ethanol production). Fermentation at room temperature of about 25° C. compared to about 30° C. for ethanol production has proven advantageous.

Especially preferred is the use of such a culture technique with a microorganism which has been selectively adapted and isolated for the preferential production of levan under such conditions, e.g. by repeated subculture and selection of a levan-producing microorganism in increasing concentrations of sucrose under the above conditions. Presently preferred for such applications is a strain of *Zymomonas mobilis* which has been described by E. L. Dally in "Plasmid Studies in *Zymomonas mobilis*", Master's Thesis, Rutgers, The State University of New Jersey, New Brunswick, NJ (1982), particularly a variant thereof which has been deposited with the American Type Culture Collection, Rockville, Maryland 20850 as ATCC Strain No. 39,985.

The microorganism is cultivated under otherwise conventional nutrient growth conditions which may be modified to enhance the formation of levan by techniques known to those skilled in the art, e.g as described in European Patent Application Publication No. 0112661-A2 published July 4, 1984. Additionally, the microbial cells can be in suspension or immobilized onto a water-insoluble support, e.g. as described in Kim et al. U.S. Pat. No. 4,384,044. After about 72 hours, fermentation can be terminated by removal or sterilization of the microorganisms and the levan recovered by cold ethanol precipitation, after which excess moisture is removed by drying, preferably to a moisture content of less than 10% by weight, and especially to less than about 2% by weight, e.g. by freeze-drying.

The effect of levan on colloidal systems has been evaluated in conjunction with a standard protein in model disperse systems to determine if the polysaccharide was effective at improving the initial formation and, more importantly, the kinetic stability of dispersed emulsions and foams formed using standard proteins.

Figure 1:
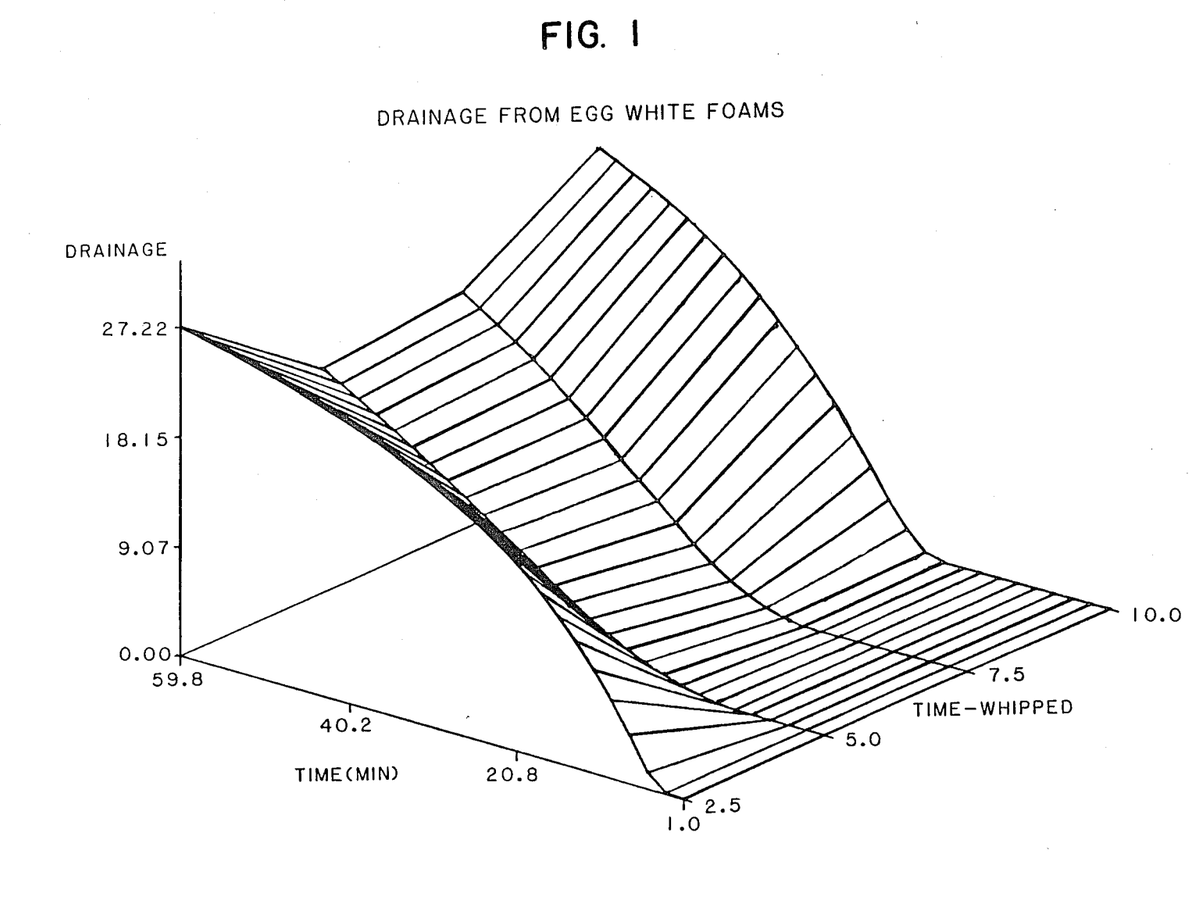

The values obtained for EAI and colloid stability are critically dependent on the measuring system employed. For all values used herein, foam formation and stability were monitored using a whipping method developed for the USDA Northeast Regional Project on Protein Functionality. 50 ml solutions of 5% BSA protein solution (0.1M phosphate pH 7.0), with or without various concentrations of the added levan, were whipped for 10 minutes at speed 13 in a Sunbeam I-125 mixer. Foam stability was measured by the weight of liquid drained from the foam and monitored continuously using an electrobalance and Apple computer. The sensitivity of the method is illustrated by the characterization of the overwhelming of egg white proteins (FIG. 1).

Results to date on the effects of the levan polysaccharide on modelled colloidal food systems suggest that this molecule, at very low levels, is able to significantly modify the physical properties of the system. Both emulsion and foam stability were improved by the presence of less than 0.05% levan in the aqueous phase. Evidence to date also suggests that these effects are not due solely to a nonspecific increase in bulk aqueous viscosity; rather, the levan appears to interact with the protein component and significantly improve its interfacial properties. These preliminary results have not described the precise mechanism by which the dramatic alterations in colloidal stability are developed, which are at present not fully known. Subsequent analyses on the model systems and the associations formed between the levan and other components present can be used to identify the basis for the physical alterations and readily suggest other food applications for this compound.

Based on the above properties, it will be appreciated tat the levan produced according to the present invention has properties which render it useful in a wide variety of emulsification applications which are limited essentially only by the molecular weight, lack of charge, and degree of branching in the levan molecule. The molecular weight can be tailored to a desired range by controlling fermentation parameters (e.g. time, temperature and ionic strength; see T. Tanaka et al., J. Biochem. 85 (1): 287–293, 1979) and by the choice of a microorganism employed, while the uncharged nature of the molecule is an inherent property which can, if desired, be modified by forming salts, e.g. as described in Heinz et al. U.S. Pat. Nos. 3,413,284 and 3,524,847 and Horst U.S. Pat. No. 3,380,999. These properties would appear to prevent its use in compositions such as drilling muds or the like which would be subject to high shear forces and heat, tending to degrade the molecule. The levan molecules produced in accordance with the present invention are essentially linear but can contain varying degrees of branching, generally less than 20% and more usually less than about 10%; this property has not yet been fully explored.

It will nonetheless be apparent that the levan polymers have wide industrial application as emulsifying and emulsion-stabilizing agents, particularly in foods, beverages, pharmaceuticals, dentifrices, and cosmetics. They are not sweet and have essentially no taste, and by virtue of their high molecular weight will not pass into the bloodstream without first being degraded in the digestive tract. They are particularly valuable in stabilizing protein emulsions, especially milk and other dairy products such as ice cream, sherbert, yogurt, custards, ice lollie, cheese and cheese products, etc., and especially in whipped emulsions such as dessert toppings, salad dressings and the like, as well as beverages such as milk shakes, orange drinks, etc. They can be used to enhance the stability of gelatinized animal food products analogous to K. Buckley et al. U.S. Pat. No. 4,143,171 and of meat and vegetable food products analogous to J. R. Mitchell et al. U.S. Pat. No. 4,143,172. They can be used to stabilize fruit and vegetable products, e.g. formed fruit structures such as "Fruit Roll-Ups", souffles, etc. In general, the levans produced according to the present invention can be applied in those industrial applications known for the widely used natural product gum arabic, as reviewed by J. Adrian et al, "Chemical and Physiological Properties of Thickening and Gelling Additives" Revue Francaise de Dietetique 23 (88): 3 -25 (1979) and the references cited therein, including electrocoating and other applications in the electronics and photography industry, e.g. see Crandall et al., U.S. Pat. No. 3,137,575.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Preparation of Microorganism

The applications described herein are based upon the use of a molecule with a weight average molecular weight of 10 to 20 million, as determined by gel filtration chromatography using Bio-Rad "Biogel" agarose having a molecular weight exclusion limit of 15 million using bacterial cells as void markers. It would be difficult to produce such a large molecular weight species through column chromatography of sucrose by an immobilized levan sucrase enzyme. The traditional bacterial fermentation of sucrose by strains of *Aerobacter levanicum* results in only 1.3 to 1.5 grams of levan per 100 milliliters of fermentation broth of the final levan product (Methods in Enzymology 8: 161–165, 1966). Production of levan by the bacterial fermentation of 2% sucrose by wildtype (or genetically unaltered) strains of *Zymomonas* results in only 0.2 to 0.3 grams of levan product per 100 milliliters of fermentation broth (Biochem. J. 98:804–812, 1966). This represents the utilization of only 2% of the total sucrose substrate present. However, from Table 1, one can see that an efficient wildtype strain in 15% sucrose produces 2.4 grams/100 ml compared with genetically modified and selected progeny which produce 3.4, 2.9 and 2.9 grams/100 ml respectively.

TABLE 1

| Strain | Levan produced (g/100 ml) | % Available Fructose Converted to Levan |
| --- | --- | --- |
| GRC 4-15 | 2.4 | 51.4 |
| GRC 4-57 | 3.4 | 72.1 |
| GRC 4-58 | 2.9 | 60.1 |
| GRC 4-59 | 2.9 | 62.1 |

Strain GRC 4-57 has been serially passaged in 15% sucrose and Difco yeast extract to allow additional adaptation to high concentrations of sucrose. A progeny strain has been isolated from strain GRC 4-57 which has resulted in the production of 4.0 to 5.0 grams of levan/100 ml of fermentation broth. This strain, GRC 4-57A, is capable of production of levan at levels not previously reported in the scientific literature. This strain has been deposited with the American Type Culture Collection, Rockville, Md. 20850 USA and bears the designation *Zymomonas mobilis* ATCC 39,985.

EXAMPLE 2

Preparation of Levan Polymer

Using a 25 liter fermentation tank containing an aqueous medium of 15% table sugar and 0.25% Amberex 510 yeast extract, *Zymomonas mobilis* ATCC 39,985 was inoculated (10% by volume) at room temperature under agitation (tip speed 130 feet/minute) without any extraneous pH control. After a seed time of about 48 hours, fermentation was continued for about 72 hours, giving a yield of about 35 g/l in the broth.

Because of its intended use in food applications, the harvested broth was continuously fed through a Sharples T-1 centrifuge at about 23,000 rpm for clarification and removal of cellular debris. The clarified broth was then mixed in a 1:3 ratio with ethanol and allowed to set in a cold room at about 4° C. for 36 hours, during which time the levan product precipitated and formed a gelatinous mass on the sides and bottom of the container. After recovering the ethanol for subsequent usage, the recovered levan was freeze-dried in a lyophilizer and the dried product (pseudo-crystal plates) was then ground through a mill to the desired particle size, e.g. of 0.1–3 mm average diameter.

The levan was readily soluble in water, forming a gel at a concentration of about 33%. The polysaccharide was found to be difficult to completely solubilize in buffer at various pH's; however, it readily formed a slightly turbid suspension up to high concentrations. This suspension was used at the specified concentrations for subsequent analyses in Examples 3–5.

EXAMPLE 3

Emulsification Activity and Stability

Figure 2:
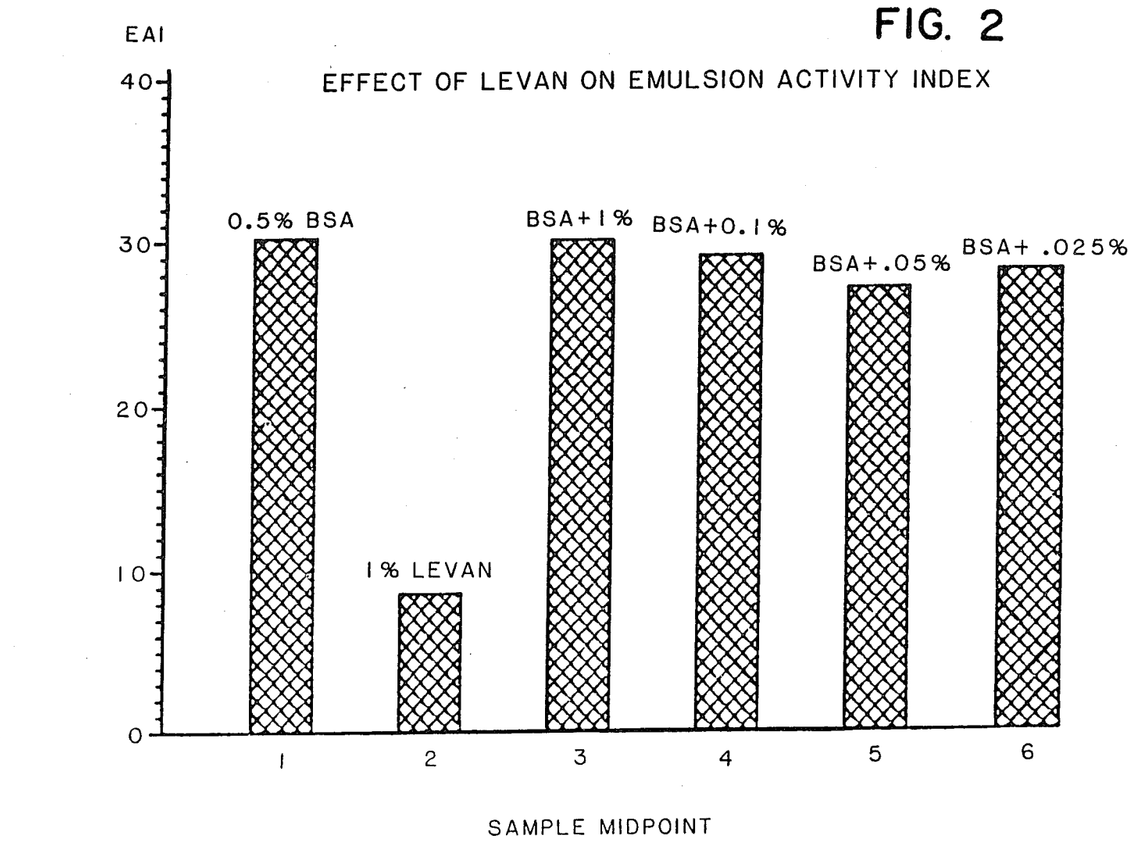

The emulsification activity indices for BSA, the levan, and combinations of each are shown in FIG. 2. The EAI estimates the total surface area of emulsion formed using a given agitation. Bovine serum albumin is generally considered to produce an intermediate level of emulsion. BSA solutions alone at 0.5% concentration formed an emulsion yielding a mean surface area of 30.3 square meters/gm. Levan by itself was a conspicuously poor emulsifier, yielding total surface areas less than 10 square meters/gm at 1% concentration. The addition of the levan to solutions of BSA did not appear to significantly affect the emulsifying *ability* of the protein under these conditions, i.e., the levan neither promoted nor prevented the BSA solution from forming an emulsion.

Emulsification activity and stability were measured using the technique described by Pearce, K. N. and Kinsella, J. E., Emulsifying Properties of Proteins: Evaluation of a Turbidimetric Technique, J. Agric. Food Chem., 26(3): 716–23, 1978. The standard protein solution consisted of 0.5% bovine serum albumen (BSA, fraction V, Sigma) in 0.1M phosphate buffer pH 7.0. A measured amount of pure peanut oil and aqueous protein and/or polysaccharide solution (10 and 30 ml respectively) were homogenized using a blender maintained at 25° C. for 10 seconds. Turbidity was measured at 500 nm using a Spectronic 700 spectrophotometer. The emulsion activity index (EAI) was calculated using the formula $EAI = 2T/OC$ where T is the turbidity, C is the weight of protein per unit volume of the aqueous phase and O the volume fraction of dispersed oil phase. Emulsion stability was determined from the decrease in absorbance with time.

EXAMPLE 4

Kinetic Stability of Emulsions

Figure 3:
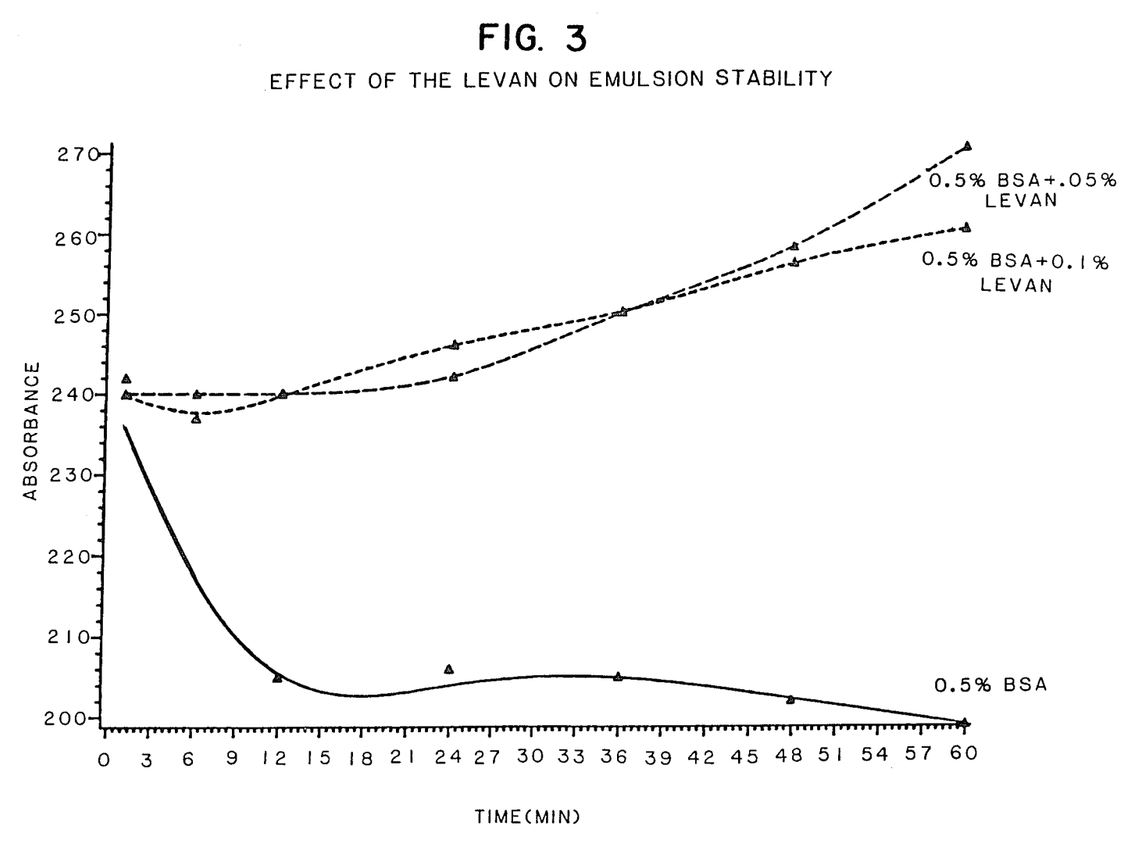

The effect of the levan on the kinetic stability of these emulsions is shown in FIG. 3. The presence of the levan had a profound effect on the aging of the emulsion. Whereas 60 minutes standing time resulted in a 25% decrease in the total surface area of the pure BSA emulsions, over this same time period the emulsions prepared with as little as 0.05% of the levan were found to actually increase in absorbance. While this increase is not likely to be due to an actual increase in surface area of the emulsions, but rather an alteration in the colloidal state of the polysaccharide, these data imply a significant improvement in the stability of the emulsion This improvement is not solely due to an increase in the viscosity of the continuous aqueous phase, since the effect is not dramatically concentration dependent for those concentrations tested.

Figure 4:
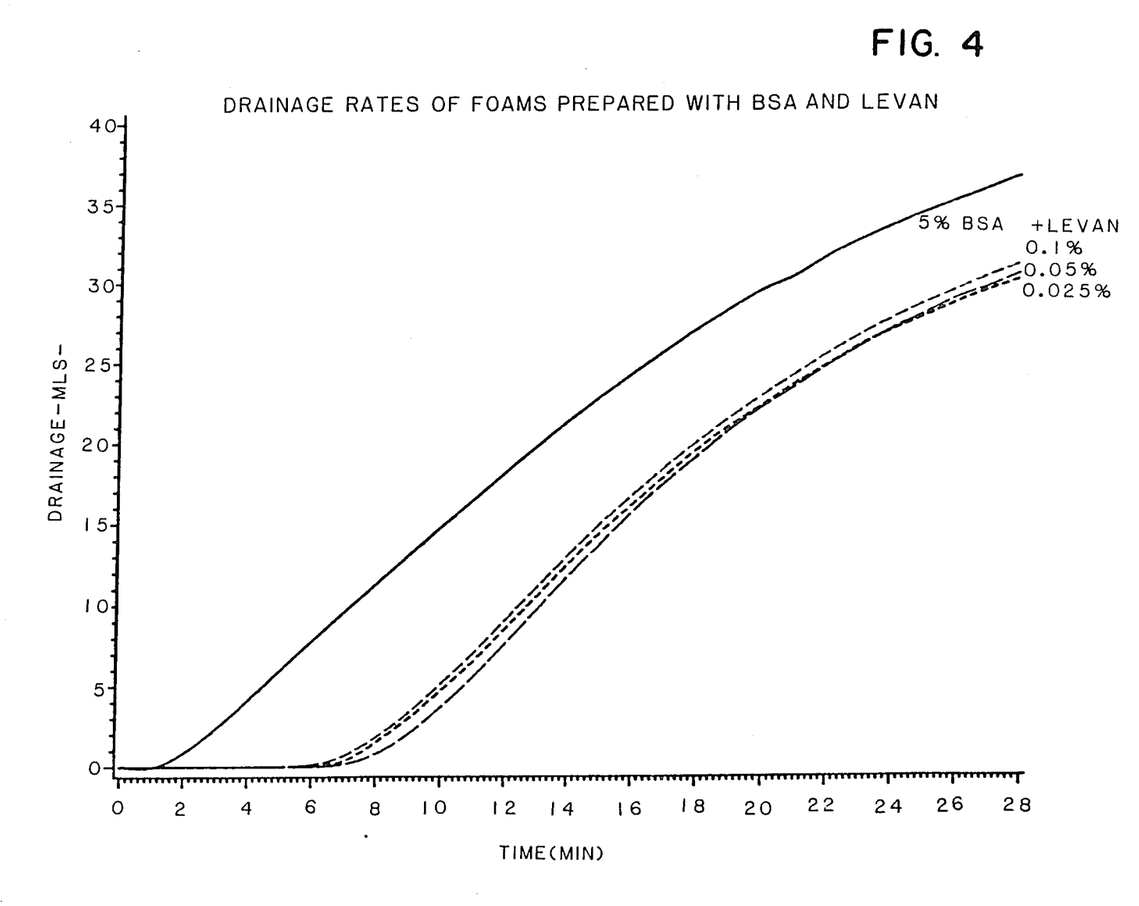

The effect of the addition of levan to BSA on the foam stability was also dramatic, as shown in FIG. 4. The addition of as little as 0.025% polysaccharide exerted a significant improvement in the drainage stability of the foams. This was clearly not solely related to the alteration of the continuous phase viscosity for the same reason that the effect was not strongly concentration dependent. This suggests that the levan is able to alter the surface activity of the protein solution in such a way as to improve the overall stability of foams prepared from them. Since the process of drainage is a highly complex interaction of several rheological and colloidal parameters, significantly more information would be required to establish the precise mechanism by which the levan is exerting the beneficial effects.

EXAMPLE 5

Foam Activity

Bovine serum albumin is also an intermediate activity foaming protein. While 5% solutions of BSA will readily form a foam, this is generally quite unstable and collapses within 30 minutes. BSA is thus an excellent model protein to study the effects of protein and solution modifications on foaming properties. The levan had little foaming activity of itself and in fact was unable to generate a measurable overrun after 20 minutes of whipping. However, addition of the levan had a significant effect on the foams produced from 5% BSA solutions.

Although the overrun was not significantly altered, the appearance of the foams was quite different, with levan-containing foams noticeably whiter, drier and of a finer texture. This suggested a smaller bubble size distribution in those foams produced from BSA in the presence of the levan.

EXAMPLE 6

Molecular Weight Determination by Light Scattering

The weight-average molecular weight (Mw) has been calculated using samples of a polyfructose polymer produced according to the process of Example 2 but recovered with a horizontal decanting type centrifuge using the technique of light scattering. This methodology is well established and described in general texts [Williams and Williams, Basic Physical Chemistry for the Life Sciences (Second Edition), pages 384–391 (W. H. Freeman and Company, San Francisco, 1973); and Aspinall, Ed., the Polysaccharides, Vol. 1, pages 217–219 (Academic Press, New York, 1982)] and other references J. B. Robbins et al., Pediatric Res. 7:103–110 (1973) and P. Doty et al., Advan. Protein Chem VI:35 (1951). This methodology is a less destructive one to the molecule than the method of exclusion gel chromatography which was used to determine the weight-average molecular weight of this polymer and described in the previous Examples.

The weight-average molecular weight of this polymer as determined by light scattering is approximately 980 million Daltons or roughly one billion Daltons. This molecular weight represents the largest weight-average molecular weight of a polymer produced by a microbiological process in vitro currently reported.

EXAMPLE 7

Bioavailability of Polyfructose Polymer

A sample of the polyfructose polymer of Example 6 was used to determine its bioavailability in the rat animal mode. Eight Sprague-Dawley rats were fasted overnight before being fed a single oral dose of two (2.0) milliliters per one hundred (100) grams of animal body weight of a twenty (20%) percent solution of the polymer in water. Blood glucose concentrations were determined from sub-orbital samples of rat blood obtained according to a schedule appearing in the table below.

These data indicate that this polymer in a water solution fed by mouth to rats is rapidly bioavailable. The blood glucose levels rose from an average fasting baseline level of 103 milligrams per deciliter (mg/dl) to an average of 148 mg/dl within fifteen (15) minutes of ingestion of the polymer by the test animals. This level gradually receded to an average baseline level within two hours of ingestion, as shown in the following table:

| GLUCOSE LEVELS (mg/dl) AT POST-ADMINISTRATION TIMES FOR POLY-LEVULAN | | | | | | |
|---|---|---|---|---|---|---|
| Sex | Weight | 0 min. | 15 min. | 30 min. | 1 hour | 2 hours |
| M | 243 | 104 | 161 | n.d.* | 108 | n.d. |
| M | 237 | 88 | 132 | n.d. | 164 | n.d. |
| F | 201 | 112 | 155 | n.d. | 141 | n.d. |
| F | 205 | 103 | 144 | n.d. | 125 | n.d. |
| M | 259 | 101 | n.d. | 133 | n.d. | 96 |
| M | 265 | 92 | n.d. | 134 | n.d. | 93 |
| F | 2200 | 114 | n.d. | 132 | n.d. | 109 |
| F | 202 | 108 | n.d. | 132 | n.d. | 108 |
| Mean | 227 | 193 | 148 | 133 | 135 | 102 |

| GLUCOSE LEVELS (mg/dl) AT POST-ADMINISTRATION TIMES FOR POLY-LEVULAN -continued | | | | | | |
|---|---|---|---|---|---|---|
| Sex | Weight | 0 min. | 15 min. | 30 min. | 1 hour | 2 hours |
| ± S.D. | 28 | 9 | 13 | 1 | 24 | 8 |

*n.d. = not determined

The bioavailability of this polymer allows for its use in food products and as pharmaceutical aids such as tablet coatings, solution viscosifiers, and emulsion stabilizers.

EXAMPLE 8

Stabilization of Cooked Ovalbumin Proteins with Polyfructose Polymer

Samples of the polyfructose polymer of Example 6 were used to stabilize protein emulsions that have been denatured with heat such as found in meringues and souffles. Four (4) cheese souffles were prepared and contained no or varying concentrations of the polyfructose polymer using a standard recipe described below.

Each souffle was prepared by adding the following ingredients to a small sauce pan and heating until a sauce-like consistency was obtained: 0.25 cup butter; 0.25 cup flour; 0.5 teaspoon of salt; 1.0 cup of milk; 1.0 cup (4.0 ounces) of shredded cheddar cheese; and 4 egg yolks. Cream of tartar was not used in this recipe, although traditionally it is used to stabilize egg white foams probably by decreasing the alkaline pH of the egg white to a neutral pH.

At this same time, four egg whites were mechanically whipped at high speed in a stainless steel bowl to produce a stiff foam or ovalbumin protein emulsion containing either: no polyfructose; 1.0 tablespoon (2.0 grams); 2.0 tablespoons (4.0 grams); or 5.0 tablespoons (10 grams) of polyfructose. Because the average total weight of all ingredients except polyfructose was 770 grams, the final concentrations of polyfructose used above and expressed as a percentage of the total weight were 0.25%, 0.50% and 1.25% respectively.

The whipped egg whites were then folded into the egg yolk-cheese sauce previously prepared above. This resulting mixture was then spooned into a standard 2.5 quart souffle dish.

Each souffle was baked in a preheated oven at 325. Fahrenheit for exactly 45 minutes. Each souffle was immediately removed from the oven and the height of the dome of the souffle was measured (zero minutes). The surface area of the dome was calculated by the formula: $A = \pi(h^2 + r^2)$. Where A is the surface area; h is the height of the souffle above the rim of the dish; and r is the radius of the dish, which is a constant for these calculations, and is equal to 9.5 centimeters.

The height of the dome was also measured six (6) minutes after being removed from the oven.

The souffle containing the greatest concentration of polyfructose (1.25%) demonstrated an egg white foam with the consistency of melted marshmallows. However, after baking the surface of the souffle appeared smooth, even and light tan, similar in appearance to a baked loaf of white bread. The texture of the inside of the souffle was like that of a pudding, very moist and dense. The control souffle (no Polyfructose) and souffles containing 0.25% and 0.50% Polyfructose had a typical blotched darker brown color and very uneven surface appearance. There was an apparent positive correlation amount the four souffles between an increased concentration of Polyfructose and an increased even and smooth surface. These three souffles were similar in that they had a light airy texture.

| SURFACE AREA IN SQUARE CENTIMETERS (cm$^2$) | | |
|---|---|---|
| Polyfructose Concentration: | Zero Minutes | Six Minutes |
| Souffle Control | 362 | 284 |
| Souffle with 0.25% | 637 | 284 |
| Souffle with 0.50% | 774 | 314 |
| Souffle with 1.25% | 815 | 347 |

EXAMPLE 9

Viscosity Measurements of Polyfructose Compared to Gum Arabic

Preliminary data on the viscosities of another polyfructose sample prepared according to the methods of Example 2 compared with those of Gum Arabic were determined in this Example. At concentrations of five (5) and ten (10) percent, polyfructose demonstrates a viscosity greater than that of Gum Arabic, e.g. 13.9 vs. 6.5 cps at 5% and 2210 vs. 11.6 cps at 10% concentrations and 25° C. respectively. The novel commercial applications of polyfructose utilizing the polymer as a viscosifier in food, pharmaceutical and industrial products can substitute for the more traditional Gum Arabic.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

Industrial Applicability

As can be seen from the present specification and examples, the present invention is industrially useful in providing new and improved emulsifying agents which exhibit improved emulsification and stabilization activity in a wide variety of applications such as foods, beverages, pharmaceuticals, dentifrices, and cosmetics.

What is claimed is:

1. In a process for forming a pharmaceutical, dentifrice or cosmetic disperse colloidal system in the form of an emulsion, aerosol, or foam wherein one of the phases thereof is a protein by a) dispersing the components thereof with one another to form a colloid and b) recovering the resultant colloid, the improvement which comprises:

admixing said components with a colloid-stabilizing amount of a water-soluble levan having a medium weight average molecular weight of at least 5 million as determined by gel filtration chromatography and which stabilizes colloids having an emulsion activity index (EAI) of about 3–100 determined with reference to bovine serum albumin according to the formula EAI=2T/OC wherein T is turbidity measured at 500 nm, C is the weight of emulsified protein per unit volume of the aqueous phase and O is the volume fraction of a dispersed oil phase.

2. A process according to claim 1 wherein the leven has a median weight average molecular weight of about 300–1,500 million as determined by light scattering.

3. A process according to claim 2 wherein the colloidal system has an emulsion activity index of about 20–50.

4. A process according to claim 1 wherein the colloidal system is a cosmetic.

5. In a pharmaceutical, dentifrice or cosmetic disperse colloidal system wherein the colloidal system is an emulsion, aerosol, or foam and one of the phases thereof is a protein, the improvement comprising a colloid-stabilizing amount of a water-soluble levan having a medium weight average molecular weight of at least 5 million as determined by gel filtration chromatography to form a colloid having an emulsion activity index (EAI) of about 3–100 determined with reference to bovine serum albumin according to the formula EAI=2T/OC wherein T is turbidity measured at 500 nm, C is the weight of emulsified protein per unit volume of the aqueous phase and O is the volume fraction of a dispersed oil phase.

6. A colloidal system according to claim 5 wherein the levan has a median molecular weight of about 5–25 million.

7. A colloidal system according to claim 6 having an emulsion activity index of about 20–50.

8. A colloidal system according to claim 5 wherein the disperse colloidal system is a sol.

9. A colloidal system according to claim 5 wherein the disperse colloidal system is an emulsion.

10. A colloidal system according to claim 5 wherein the disperse colloidal system is an aerosol.

11. A colloidal system according to claim 5 wherein the disperse colloidal system is a foam.

12. A colloidal system according to claim 5 wherein the disperse colloidal system is a gel.

13. A colloidal system according to claim 5 wherein the disperse colloidal system is a pharmaceutical composition.

14. A colloidal system according to claim 5 wherein the disperse colloidal system is a dentifrice.

15. A colloidal system according to claim 5 wherein the disperse colloidal system is a cosmetic.

* * * * *